(12) United States Patent
Werzowa

(10) Patent No.: US 10,772,533 B2
(45) Date of Patent: Sep. 15, 2020

(54) ADAPTIVE AUDIO THERAPY SYSTEM

(71) Applicant: Walter Werzowa, Woodland Hills, CA (US)

(72) Inventor: Walter Werzowa, Woodland Hills, CA (US)

( * ) Notice: Subject to any disclaimer, the term of this patent is extended or adjusted under 35 U.S.C. 154(b) by 0 days.

(21) Appl. No.: 16/216,031

(22) Filed: Dec. 11, 2018

(65) Prior Publication Data

US 2020/0030192 A1    Jan. 30, 2020

Related U.S. Application Data

(60) Provisional application No. 62/711,114, filed on Jul. 27, 2018.

(51) Int. Cl.
*G08B 21/04* (2006.01)
*A61B 5/08* (2006.01)
(Continued)

(52) U.S. Cl.
CPC ........ *A61B 5/0816* (2013.01); *A61B 5/02055* (2013.01); *A61B 5/02405* (2013.01);
(Continued)

(58) Field of Classification Search
CPC ........ A63F 2300/1037; A63F 2003/083; A63F 3/04; A63F 13/211; A63F 11/00; A63F 13/212; A63F 13/245; A63F 13/25; A63F 13/5255; A63F 2300/8082; B60K 28/066; B60W 2040/0818; B60W 2040/0872; B60W 2040/089; B60W 2520/00; B60W 2520/105; B60W 2520/125; B60W 2540/02; B60W 2540/22; B60W 2550/12; B60W 2550/20; B60W 2550/308; B60W 40/08; B61L 15/009; G06F 1/163; G06F 3/011; G06K 9/00845; G06Q 40/08;
(Continued)

(56) References Cited

U.S. PATENT DOCUMENTS 5,581,238 A    12/1996  Chang
5,830,235 A *  11/1998  Standley ................ A61B 5/486
                                                    606/234

(Continued)

OTHER PUBLICATIONS

PCT Search Report and Opinion for PCT/US18/65363; dated May 16, 2019.
(Continued)

*Primary Examiner* — Daniel Previl
(74) *Attorney, Agent, or Firm* — Neustel Law Offices

(57) ABSTRACT

An adaptive audio therapy system which detects and processes one or more individuals' conditions to provide adaptive, continuous audio therapy in real-time. The adaptive audio therapy system generally includes a detection device that is typically in physical contact with an individual, such as a pacifier or steering wheel. The detection device may include sensors to detect various conditions of the individual, such as heart rate, respiration rate, temperature, and the like. A computing device receives and processes the various conditions detected by the sensors. Based on the detected conditions, the computing device provides audio therapy which is adaptive to the condition of the patient and which is continuously adapted in real-time.

9 Claims, 14 Drawing Sheets

(51) Int. Cl.
*G06F 3/16* (2006.01)
*G06F 3/01* (2006.01)
*A61B 5/024* (2006.01)
*B60W 40/08* (2012.01)
*A61B 5/0205* (2006.01)
*A61J 17/00* (2006.01)

(52) U.S. Cl.
CPC ............ *B60W 40/08* (2013.01); *G06F 3/015* (2013.01); *G06F 3/16* (2013.01); *A61B 2562/06* (2013.01); *A61J 17/001* (2015.05); *B60W 2040/0872* (2013.01)

(58) Field of Classification Search
CPC ........ G06Q 10/10; G06Q 50/22; G08B 21/02; G08B 21/06; G09B 19/00; G09B 5/00; H04L 29/06; H04L 65/403; H04L 67/12; H04L 67/306; H04L 67/38; H04M 3/567; H04N 7/142; H04N 7/15; H04W 4/16; H04W 4/38; H04W 4/48; H04W 88/02; A61B 3/0285
USPC ....... 340/539.12, 576, 439, 438, 575, 539.1, 340/615, 636.11, 641, 683, 691.6, 692
See application file for complete search history.

(56) References Cited

U.S. PATENT DOCUMENTS

| | | | |
|---|---|---|---|
| 8,482,416 B2 | 7/2013 | Krans | |
| 9,135,803 B1 * | 9/2015 | Fields | ................... G06Q 40/08 |
| 9,662,266 B2 | 5/2017 | Aron | |
| 2001/0029324 A1 | 10/2001 | Walker | |
| 2006/0191543 A1 * | 8/2006 | Becker | ................ A63F 3/04 128/898 |
| 2007/0265661 A1 | 11/2007 | Coleman | |
| 2009/0149721 A1 | 6/2009 | Yang | |
| 2014/0046231 A1 * | 2/2014 | Barlow | ................ A61B 5/024 601/100 |
| 2015/0080670 A1 * | 3/2015 | Osorio | ................ A61B 5/0205 600/301 |
| 2017/0020788 A1 | 1/2017 | Malone | |
| 2017/0072162 A1 * | 3/2017 | Kim | ................ A61M 21/02 |
| 2018/0052655 A1 * | 2/2018 | Hannibal, III et al. | ................ G06F 3/165 |
| 2018/0064612 A1 | 3/2018 | Coleman | |
| 2018/0338025 A1 * | 11/2018 | Talty | ................ G10L 25/48 |

OTHER PUBLICATIONS https://www.pacif-i.io/collections/frontpage/products/smart-pacifier-in-green; Pacif-i—The Smart Pacifier Webpage; Jun. 11, 2018.
https://www.kokomole.com/; Kokomole Smart Pacifier Website; Jun. 11, 2018.
https://www.engadget.com/2015/01/05/smart-pacifier-tracks-your-baby-and-its-fever/; Engadget Webpage for Pacif-i; Jun. 11, 2018.
https://owletcare.com/; Owlet Baby Monitoring Smart Sock Website; Jun. 11, 2018.
https://www.iotcoresoft.com/iot-knowlegde-center/how-automotive-biometrics-can-help-you-predict-the-future; IoTCoreSoft Auto Biometrics Webpage; Jun. 11, 2018.

* cited by examiner

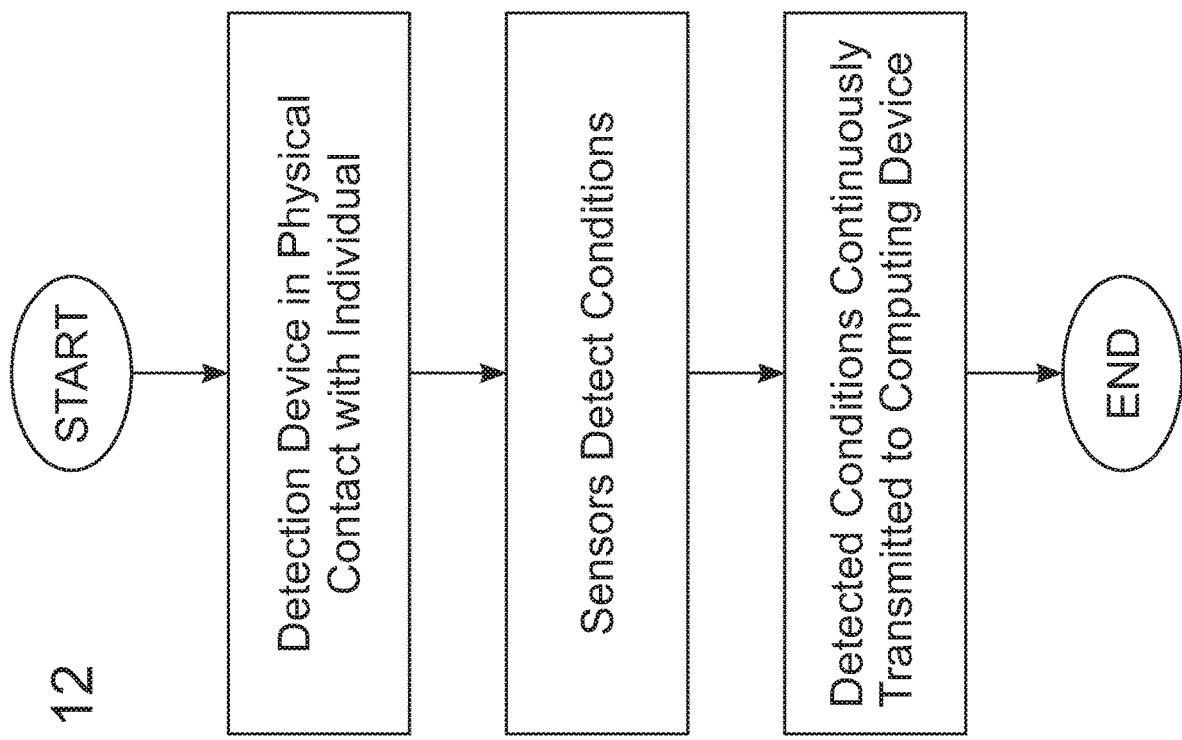

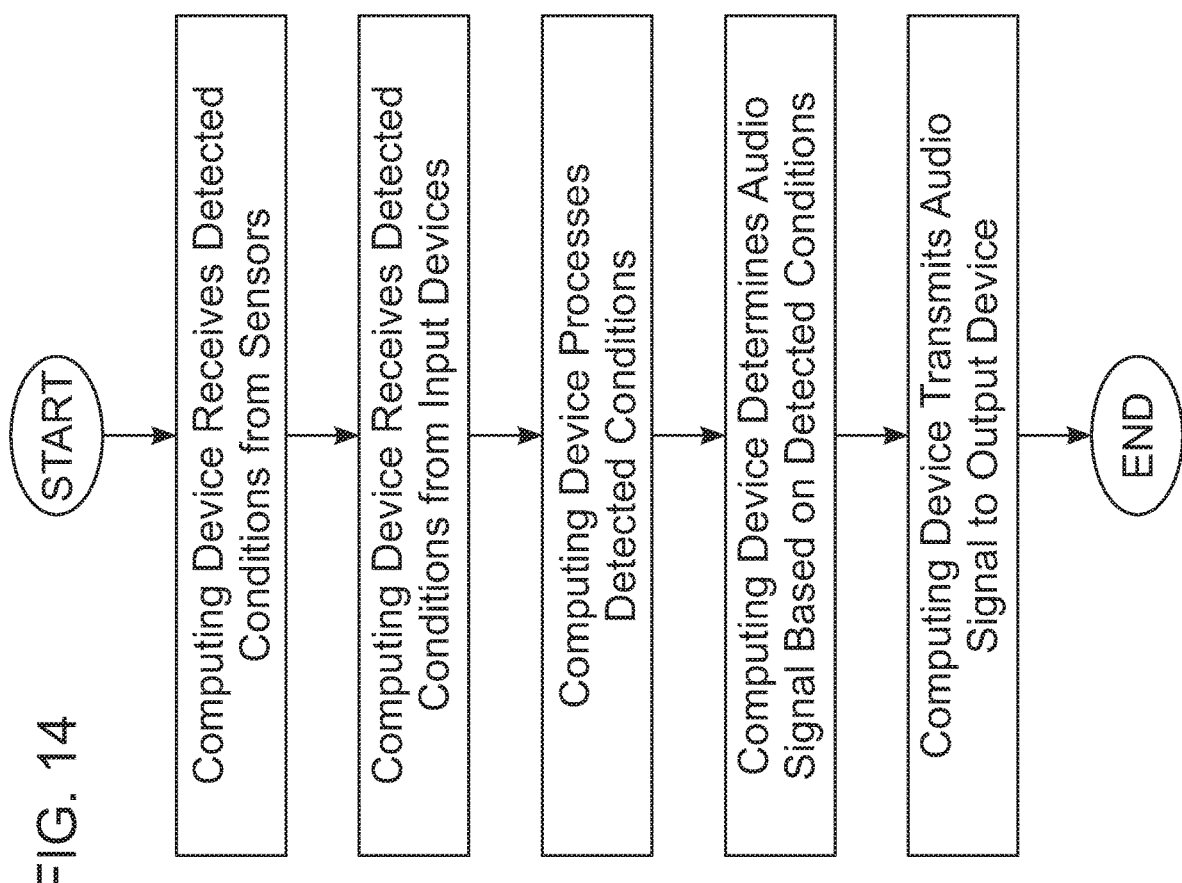

ADAPTIVE AUDIO THERAPY SYSTEM

CROSS REFERENCE TO RELATED APPLICATIONS

I hereby claim benefit under Title 35, United States Code, Section 119(e) of U.S. provisional patent application Ser. No. 62/711,114 filed Jul. 27, 2018. The 62/711,114 application is hereby incorporated by reference into this application.

STATEMENT REGARDING FEDERALLY SPONSORED RESEARCH OR DEVELOPMENT

Not applicable to this application.

BACKGROUND

Field

Example embodiments in general relate to an adaptive audio therapy system which detects and processes one or more individuals' conditions to provide adaptive, continuous audio therapy in real-time.

Related Art

Any discussion of the related art throughout the specification should in no way be considered as an admission that such related art is widely known or forms part of common general knowledge in the field.

Audio and music therapy have been in use for many years. Audio (music) therapists will often perform live music based on a patient's symptoms, illnesses, and/or diagnoses, in addition to engaging in real-time with the patient. Such therapists typically assess and interpret the patient's needs based on intuition and therapy protocols. Each patient will generally receive unique, personalized treatment based on the therapist's analysis of their condition, based on clinical research and studies. Musical therapy is taught in universities throughout the world.

However, therapists' work is not scalable. For example, it cannot be used to provide multiple personalized feeds in one room and requires human intervention and instruments (including the human voice). Availability thus depends on access to therapists, while hospitals typically need to allocate budgets to surgery/emergency and other immediate needs. Additionally, humans are prone to error and may not adequately diagnose the condition of the patient. Further, humans may spread communicable diseases and thus are not permitted in clean rooms (such as bone marrow transplant rooms) where patients in need of such therapy may be located.

Software applications have been provided which minimal functionality for music therapy. For example, a jogging application may match the tempo of a playlist to match running speed. However, such applications do not provide algorithms to change music towards tempo changes to allow healthier resting heart rate and are limited in their abilities to diagnose conditions (often based on limited or no information) and provide personalized therapies that are adaptive in real-time.

SUMMARY

An example embodiment is directed to an adaptive audio therapy system. The adaptive audio therapy system includes a detection device that is typically in physical contact with an individual, such as a pacifier or steering wheel. The detection device may include sensors to detect various conditions of the individual, such as heart rate, respiration rate, temperature, and the like. A computing device receives and processes the various conditions detected by the sensors. Based on the detected conditions, the computing device provides audio therapy which is adaptive to the condition of the patient and which is continuously adapted in real-time.

There has thus been outlined, rather broadly, some of the embodiments of the adaptive audio therapy system in order that the detailed description thereof may be better understood, and in order that the present contribution to the art may be better appreciated. There are additional embodiments of the adaptive audio therapy system that will be described hereinafter and that will form the subject matter of the claims appended hereto. In this respect, before explaining at least one embodiment of the adaptive audio therapy system in detail, it is to be understood that the adaptive audio therapy system is not limited in its application to the details of construction or to the arrangements of the components set forth in the following description or illustrated in the drawings. The adaptive audio therapy system is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

FIG. 12 is a flowchart illustrating condition detections of an adaptive audio therapy system in accordance with an example embodiment.

FIG. 14 is a flowchart illustrating audio signal transmission of an adaptive audio therapy system in accordance with an example embodiment.

DETAILED DESCRIPTION

A. Overview

Figure 1:
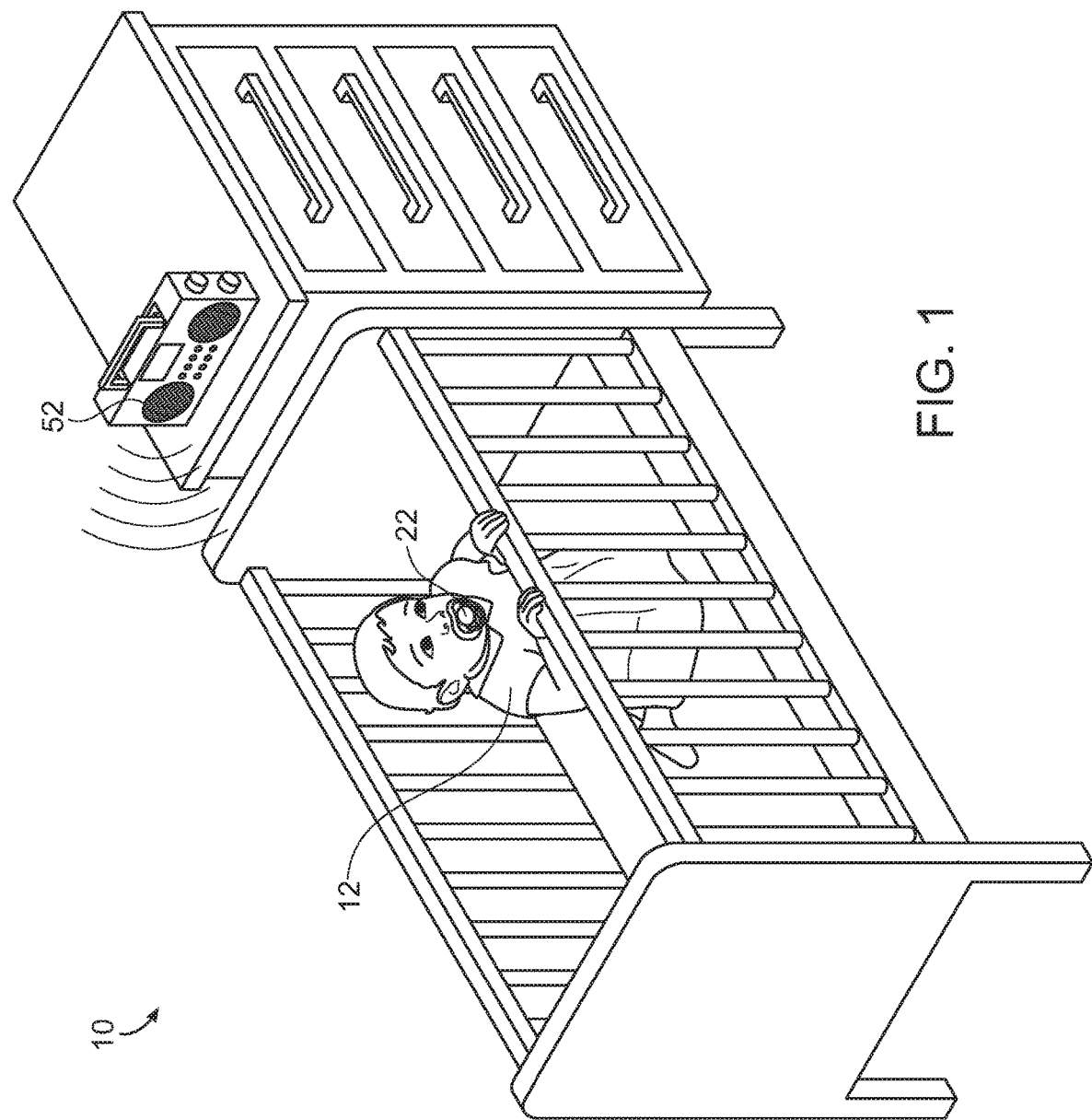
FIG. 1 is a perspective view of an adaptive audio therapy system in use with a pacifier and a speaker in accordance with an example embodiment.

An example adaptive audio therapy system 10 generally comprises a detection device 20 adapted to make physical contact with an individual 12, the detection device 20 comprising at least one sensor 40 for detecting at least one condition of the individual 12. A computing device 70 may be communicatively interconnected with the detection device 20 for processing detection data received from the at least one sensor 40 of the detection device 20; with the computing device 70 being adapted to automatically identify an audio signal based on the at least one condition detected by the sensor 40 of the detection device 20. An output device 50 may be provided for audibly playing the audio signal in real-time. The audio signal may be comprised of music or other audible tones, such as a soothing voice or nature (environmental) sounds. The audio signal may in some embodiments incorporate binaural or isochronic tones.

The output device 50 may comprise a speaker 52. The detection device 20 may comprise a pacifier 22. The at least one sensor 40 may comprise a suction sensor 41 for detecting attributes of a sucking motion applied to the pacifier 22 by the individual 12. The computing device 70 may be adapted to automatically identify the audio signal based on the sucking motion applied to the pacifier 22 by the individual 12.

The at least one sensor 40 may also comprise an oxygen saturation sensor 47 for detecting oxygen saturation of the individual 12. The at least one sensor 40 may further comprise a temperature sensor 42 for detecting a temperature of the individual 12, a heart rate sensor 44 for detecting a heart rate of the individual 12, a heart rate variability sensor 45 for detecting a heart rate variability of the individual 12, a respiration sensor 43 for detecting respiration of the individual 12, and a movement sensor 46 for detecting movement of the individual 12.

The detection device 20 may comprise a steering wheel 24. The at least one sensor 40 may comprise a grip sensor 48 for detecting a grip force applied to the steering wheel 24 by the individual 12. The computing device 70 may be adapted to automatically identify the audio signal based on the grip force applied to the steering wheel 24 by the individual 12. The at least one sensor 40 may further comprise a temperature sensor 42 for detecting a temperature of the individual 12, a heart rate sensor 44 for detecting a heart rate of the individual 12, a heart rate variability (HRV) sensor 45 for detecting a heart rate variability of the individual 12, a respiration sensor 43 for detecting respiration of the individual 12, and a galvanic skin sensor 49.

The detection device 20 may comprise a control unit 30 for controlling communication of the detected conditions to the computing device 70. The control unit 30 may comprise a microprocessor and/or a transceiver 32.

In another exemplary embodiment, the adaptive audio therapy system 10 may comprise a detection device 20 adapted to make physical contact with an individual 12; the detection device 20 comprising a plurality of sensors 40 for detecting a plurality of first conditions of the individual 12. A computing device 70 may be communicatively interconnected with the detection device 20 for processing detection data received from the sensors 40 of the detection device 20; with the computing device 70 being adapted to automatically identify an audio signal based on the first conditions detected by the sensors 40 of the detection device 20. An output device 50 may be configured for audibly playing the audio signal in real-time.

An input device 60 may be communicatively connected to the computing device 70, with the input device 60 being adapted to detect a plurality of second conditions of the individual 12. The computing device 70 may be adapted to automatically identify the audio signal based on both the first conditions detected by the sensors 40 and the second conditions detected by the input device 60.

The input device 60 may be selected from the group consisting of a heartrate monitor 62, a heartrate variability monitor 63, an electroencephalogram 64, an electrocardiogram 65, and a mobile device 66. The sensors 40 may be selected from the group consisting of a temperature sensor 42, a respiration sensor 43, a heartrate sensor 44, a heartrate variability sensor 45, a movement sensor 46, and an oxygen saturation sensor 47.

The detection device 20 may comprise a pacifier 22; with the sensors 40 being selected from the group consisting of a suction sensor 41, a temperature sensor 42, a respiration sensor 43, a heartrate sensor 44, a heartrate variability sensor 45, a movement sensor 46, and an oxygen saturation sensor 47. The detection device 20 may comprise a vehicle; with the sensors 40 being selected from the group consisting of a grip sensor 48, a tapping sensor, a galvanic skin sensor 49, a temperature sensor 42, a respiration sensor 43, a heartrate sensor 44, a heartrate variability sensor 45, a movement sensor 46, an oxygen saturation sensor 47, and a tapping sensor 59.

B. Detection Device

As shown throughout the figures, the systems and methods described herein may include a detection device 20 which is utilized to detect various conditions of an individual in physical contact with the detection device 20. The type of detection device 20 utilized may vary widely in different embodiments. The detection device 20 may comprise any physical object which may be in contact with the individual desiring adaptive audio therapy. By way of example and without limitation, the detecting device 20 could in various embodiments comprise a child's pacifier 22, a wristband, a watch, an implant, a headband, various components of a vehicle including a steering wheel, a chair, and the like.

FIGS. 1-4 illustrate an exemplary detection device 20 comprised of a child's pacifier 22. The detection device 20 should not be construed as limited by the exemplary embodiment shown in the figures. As shown in FIGS. 1-4, the pacifier 22 may be adapted to be sucked on by an individual 12 such as a child. As children often are not able to efficiently convey their physiological condition, this particular type of detection device 20 may be particularly helpful in providing adaptive audio therapy utilizing the systems and methods described herein.

The detection device 20 may include a control unit 30 which is incorporated with the detection device 20. In the case of a pacifier 22, the control unit 30 may be stored within the base of the pacifier 22. In other embodiments, the control unit 30 may be stored within the suction portion of the pacifier 22.

The control unit 30 may be adapted to process and transfer the data detected by one or more sensors 40 of the detection device 20. The control unit 30 may comprise a processing unit such as a microprocessor. By way of example, the control unit 30 may comprise an ARM processor or a system-on-a-chip. The control unit 30 will preferably be small enough to fit within the detection device 20. The figures illustrate an exemplary embodiment which utilizes a control unit 30 fit within a pacifier 20.

The detection device 20 may comprise a transceiver 32 which is adapted to communicate data from the detection device 20 to a computing device 70; with the computing device 70 being adapted to process the data detected by the one or more sensors 40 and adaptively in real-time select and alter/modify appropriate audio therapy based on the present condition of the individual 12 utilizing the detection device 20.

The transceiver 32 may be incorporated into the control unit 30 such that the control unit 30 and transceiver 32 are integral with each other. In other embodiments, the transceiver 32 may be communicatively interconnected with the control unit 30. In either case, the transceiver 32 is adapted to continuously in real-time transmit the data from the sensor(s) 40 to the computing device 70. In some embodiments, the transceiver 32 may instead comprise a transmitter adapted to send, but not to receive, data. In other embodiments, the transceiver 32 may be adapted to both send and receive data.

The manner in which the transceiver 32 transmits data may vary in different embodiments. The detection device 20 may in some embodiments be connected by wire to the computing device 70. In other embodiments, the transceiver 32 may be adapted to transmit wireless data to the computing device 70. By way of example and without limitation, the transceiver 32 may in various embodiments utilize Wi-Fi, BLUETOOTH, a communications network such as the Internet, RFID, or various other communications protocols for transmitting (or receiving) data to the computing device 70 continuously in real-time.

C. Sensor(s)

The detection device 20 may include one or more sensors 40 each adapted to detect various conditions such as biomarkers of the individual 12 using the detection device 20. The sensors 40 may each individually detect a condition or, in some cases, a single sensor 40 may itself detect multiple conditions. All of the sensors 40 will preferably be communicatively interconnected with the computing device 70 such that the computing device 70 receives data in real-time. By way of example, the sensors 40 may be wired to the control unit 30 which transmits the data to the computing device 70 in real-time.

The conditions detected by the sensors 40 will vary in different embodiments depending on the individual 12 being treated and the type of detection device 20 being utilized, among other factors. By way of example, in embodiments in which the detection device 20 comprises a pacifier 22, the sensors 40 may be adapted to detect conditions such as vitals, sucking motion, motion patterns, temperature, heart rate, heart rate variability (HRV), respiratory function, movement patters, and oxygen saturation. In other embodiments in which the detection device 20 does not comprise a pacifier 22, conditions such as sucking motion may be omitted.

Figure 9:
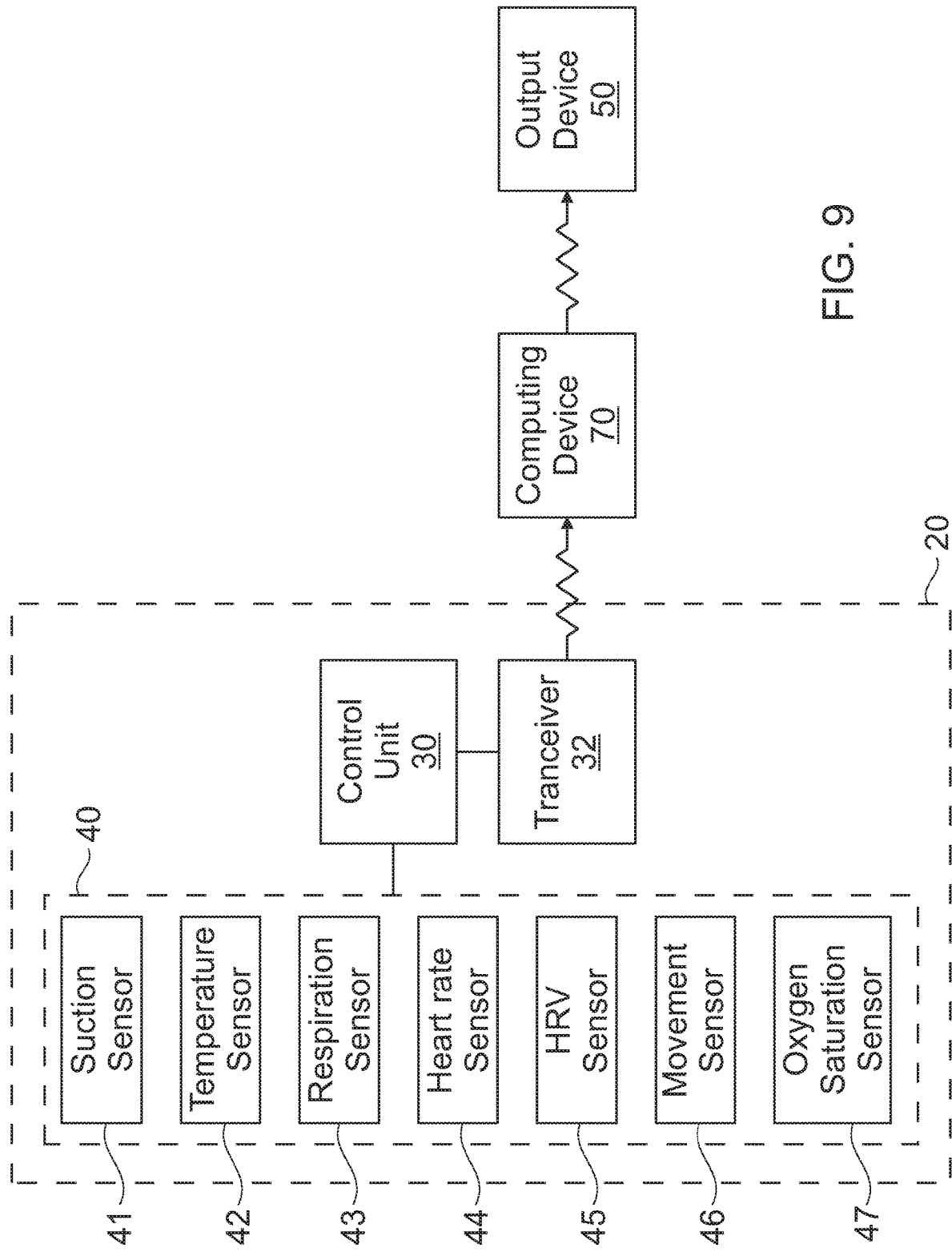
FIG. 9 is a block diagram of an adaptive audio therapy system in accordance with an example embodiment.

FIG. 9 illustrates an exemplary configuration of sensors 40 for use with a pacifier 22. It should be appreciated that more or less sensors 40 may be included depending on the individual 12 and the audio therapy desired to be applied. In the exemplary embodiment shown in FIG. 9, the detection device 40 is illustrated as including a suction sensor 41, temperature sensor 42, a respiration sensor 43, a heart rate sensor 44, a heartrate variability sensor 45, a movement sensor 46, and an oxygen saturation sensor 47.

As shown in FIG. 9, the detection device 20 may comprise a suction sensor 41 which is adapted to detect various attributes of a sucking motion applied to the pacifier 22 by an individual 12 being treated. The suction sensor 41 may be adapted to detect speed of suction motions applied to the detection device 20, force applied by suction motions applied to the detection device 20, and rate of suction motions applied to the detection device 20, among other things.

Utilizing these detected conditions from the suction sensor 41 (and other sensors 40 if included), the computing device 70 may determine a stress level of the patient 12 and the efficacy of audio therapy being applied. For example, a sudden increase in suction motions being applied to the detection device 20 may be indicative of rising stress. In contrast, a gradual decrease of suction motions may be indicative of lowering stress. These conditions may be utilized by the computing device 70 to adaptively configure the audio signal to match the mood/condition of the patient at any given time.

As shown in FIG. 9, the detection device 20 may comprise a temperature sensor 42 which is adapted to detect a body temperature of the individual 12 being treated. The temperature sensor 42 will generally be positioned on the detection device 20 such that the temperature sensor 42 is in contact with the patient 12 to get a temperature reading. The control unit 30 or computing device 70 may be adapted to continuously track temperature readings from the temperature sensor 42 to detect increases or decreases in patient 12 temperature.

Utilizing these detected conditions from the temperature sensor 42 (and other sensors 40 if included), the computing device 70 may determine aspects of the patient's health and the efficacy of treatments being applied. A higher temperature or a rise in temperature may be indicative of illness or stress. A normal temperature or a lowering in temperature may be indicative of recovery. These conditions may be utilized by the computing device 70 to adaptively configure the audio signal to match the wellbeing of the patient at any given time.

As shown in FIG. 9, the detection device 20 may comprise a respiration sensor 43 which is adapted to detect respiration rate of the patient 12 being treated. The respiration sensor 43 will generally be positioned on the detection device 20 such that the respiration sensor 43 is in contact with the patient 12 or in the path of the patient's 12 airway so as to detect respiration by the patient 12. The control unit 30 or computing device 70 may be adapted to continuously track respiration readings from the respiration sensor 43 to detect increases or decreases in patient 12 respiration rates.

Utilizing these detected conditions from the respiration sensor 43 (and other sensors 40 if included), the computing device 70 may determine aspects of the patient's health and the efficacy of treatments being applied. A higher respiration rate or a sudden increase in respiration rate may be indicative of stress. A normal respiration rate or a decrease in respiration rate may be indicative of calming. These conditions may be utilized by the computing device 70 to adaptively configure the audio signal to match the wellbeing of the patient at any given time.

As shown in FIG. 9, the detection device 20 may comprise a heartrate sensor 44 which is adapted to detect a heartrate of the patient 12 being treated. The heartrate sensor 44 will generally be positioned on the detection device 20 such that the heartrate sensor 44 is in contact with a pulse of the patient 12. The control unit 30 or computing device 70 may be adapted to continuously track heartrate readings from the heartrate sensor 44 to detect increases or decreases in patient 12 heartrates.

Utilizing these detected conditions from the heartrate sensor 44 (and other sensors 40 if included), the computing device 70 may determine aspects of the patient's health and the efficacy of treatments being applied. A higher heartrate or a rise in heartrate may be indicative of stress. A normal heartrate or a lowering in heartrate may be indicative of lowering stress. Alternatively, a heightened heartrate may be indicative of exercise being performed. These conditions may be utilized by the computing device 70 to adaptively configure the audio signal to match the wellbeing of the patient at any given time.

As shown in FIG. 9, the detection device 20 may comprise a heartrate variability (HRV) sensor 45. The HRV sensor 45 will generally be positioned on the detection device 20 such that the HRV sensor 45 is in contact with a pulse of the patient 12. The control unit 30 or computing device 70 may be adapted to continuously track HRV readings from the HRV sensor 45 to detect changes.

Utilizing these detected conditions from the HRV sensor 45 (and other sensors 40 if included), the computing device 70 may determine aspects of the patient's health and the efficacy of treatments being applied. A higher HRV reading may be indicative of illness or stress. A normal HRV reading may be indicative of recovery. HRV may also be utilized to determine whether the patient 12 is exercising. These conditions may be utilized by the computing device 70 to adaptively configure the audio signal to match the wellbeing of the patient at any given time.

As shown in FIG. 9, the detection device 20 may comprise a movement sensor 46 which is adapted to detect movement of the patient 12. The movement sensor 46 will generally be positioned on the detection device 20 to detect movements of the detection device 20. The control unit 30 or computing device 70 may be adapted to continuously track movement readings from the movement sensor 46 to detect movements of the patient 12.

Utilizing these detected conditions from the movement sensor 46 (and other sensors 40 if included), the computing device 70 may determine aspects of the patient's health and the efficacy of treatments being applied. Sudden or frantic movements may be indicative of stress. Lack of movement may be indicative of a calm disposition, or sleep. These conditions may be utilized by the computing device 70 to adaptively configure the audio signal to match the wellbeing of the patient at any given time.

As shown in FIG. 9, the detection device 20 may comprise an oxygen saturation sensor 47 which is adapted to detect oxygen saturation levels of the patient 12. The oxygen saturation sensor 47 will generally be positioned on the detection device 20 such that the oxygen saturation sensor 47 may contact a patient 12 for a proper reading. The control unit 30 or computing device 70 may be adapted to continuously track oxygen saturation readings from the oxygen saturation sensor 47 to detect changes.

Utilizing these detected conditions from the oxygen saturation sensor 47 (and other sensors 40 if included), the computing device 70 may determine aspects of the patient's health and the efficacy of treatments being applied. Low oxygen saturation readings can be indicative of health problems. These conditions may be utilized by the computing device 70 to adaptively configure the audio signal to match the wellbeing of the patient at any given time.

Figure 5:
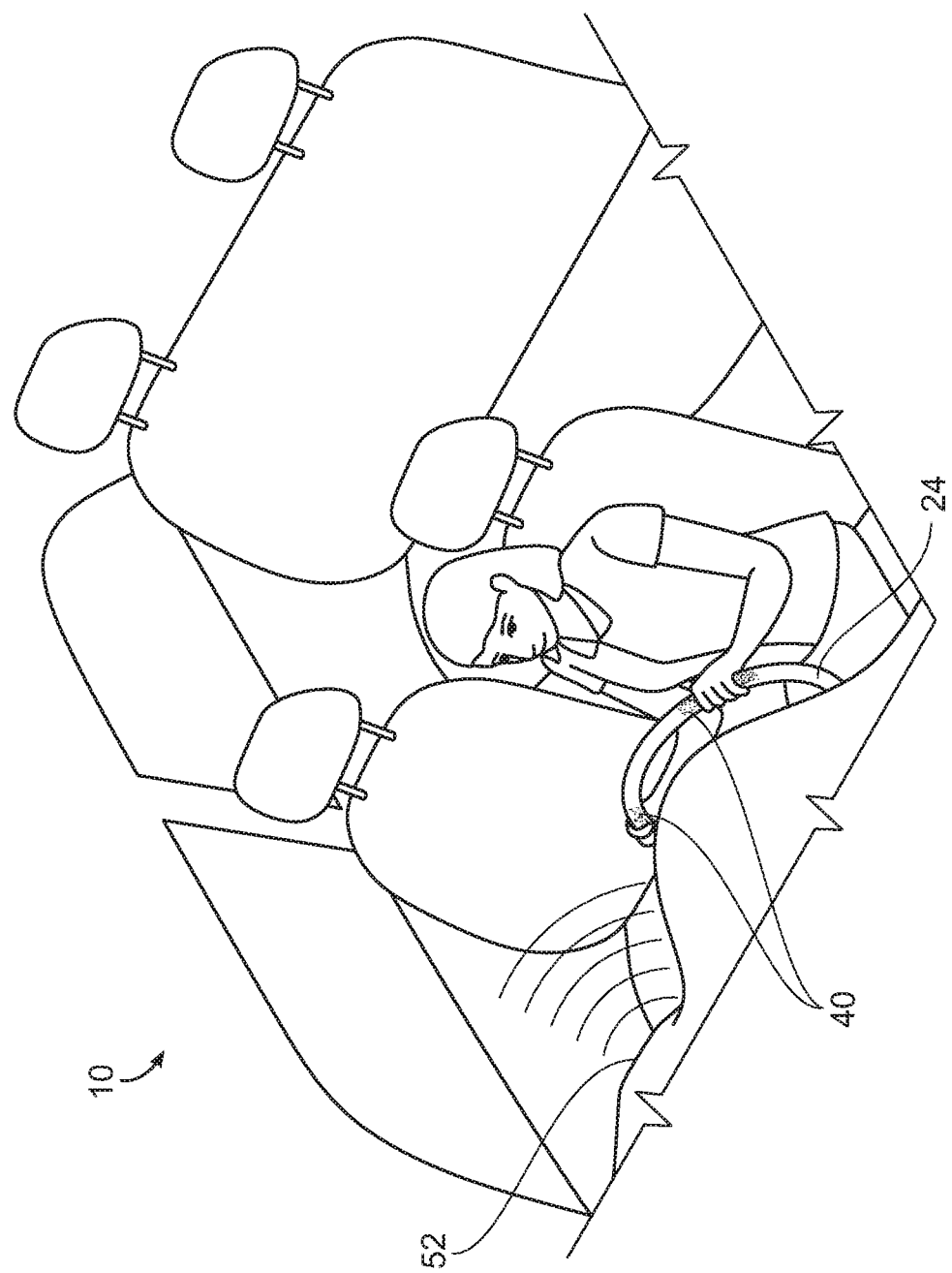
FIG. 5 is a perspective view of an adaptive audio therapy system in use with a vehicle steering wheel and a speaker in accordance with an example embodiment.
Figure 10:
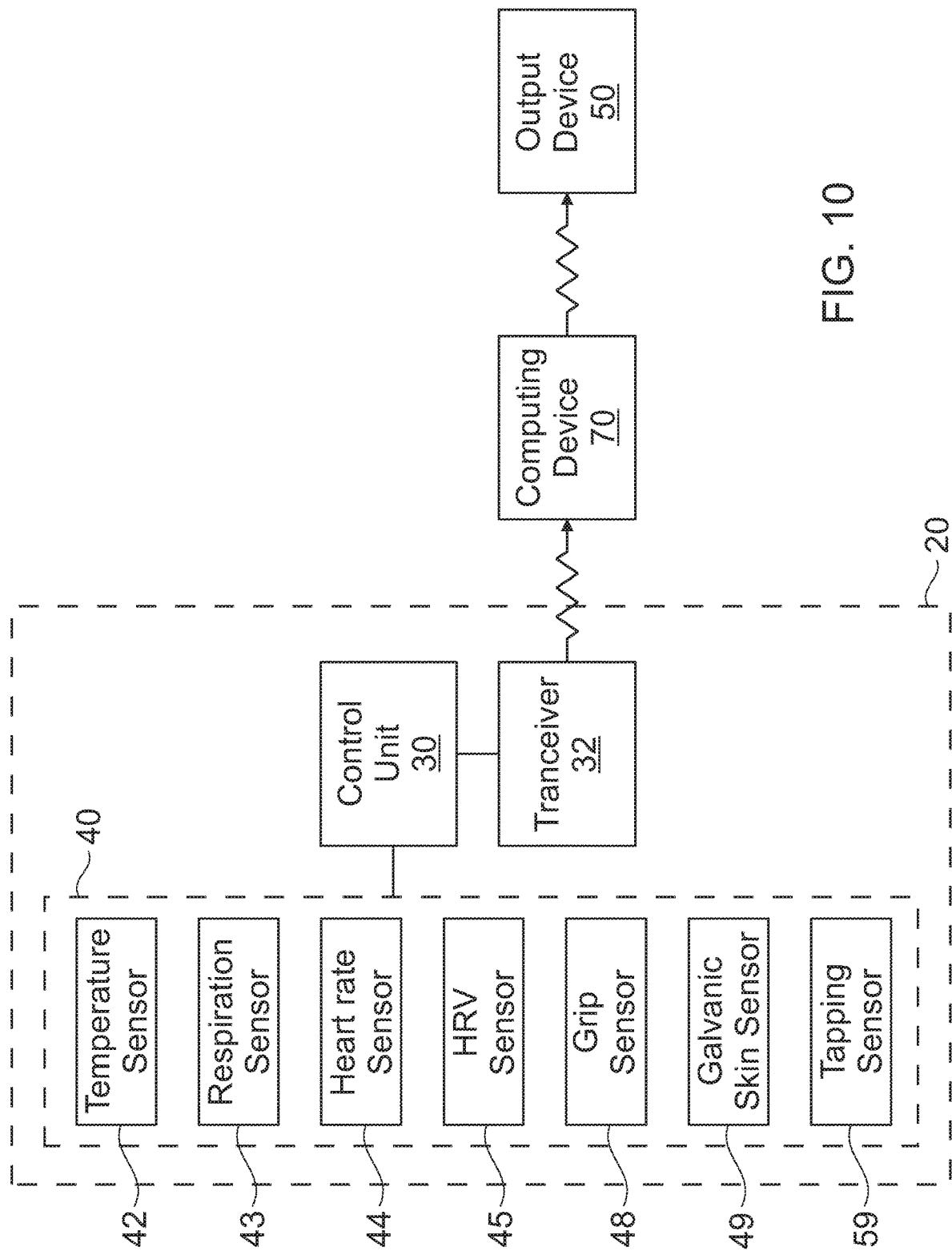
FIG. 10 is a block diagram of an adaptive audio therapy system in accordance with an example embodiment.

FIG. 10 illustrates another exemplary embodiment in which the detection device 20 is incorporated in a vehicle, such as a steering wheel 24, gear shift, arm rests, seats, or any other location in the vehicle where a patient 12 would place a portion of his or her body. FIG. 5 illustrates a detection device comprised of a steering wheel 24, with sensors 40 being positioned on the steering wheel 24 itself.

A variety of sensors 40 may be utilized in connection with such an embodiment. In the exemplary embodiment shown in FIG. 10, the detection device 40 is illustrated as including a temperature sensor 42, respiration sensor 43, heart rate sensor 44, HRV sensor 45, grip sensor 48, galvanic skin sensor 49, and tapping sensor 59. Various combinations of sensors 40 may be utilized, and FIG. 10 should not be construed as limiting in scope.

As shown in FIG. 10, the detection device 20 may comprise a grip sensor 48 which is adapted to detect grip strength applied to the detection device 20, such as a steering wheel 24. The grip sensor 48 will preferably be positioned on the detection device 20 at a position which is grasped by a patient 12, such as the steering wheel 24 as shown, or a gear shift. The control unit 30 or computing device 70 may be adapted to continuously track grip strength readings from the grip sensor 48 to detect changes.

Utilizing these detected conditions from the grip sensor 48 (and other sensors 40 if included), the computing device 70 may determine aspects of the patient's health and the efficacy of treatments being applied. High grip strengths, or sudden increases thereof, may be indicative of stress. These conditions may be utilized by the computing device 70 to adaptively configure the audio signal to match the wellbeing of the patient at any given time.

As shown in FIG. 10, the detection device 20 may comprise a galvanic skin sensor 49 which is adapted to detect electrodermal activity of the patient 12. The galvanic skin sensor 49 will thus preferably be positioned on the detection device 20 at a position which is in contact with the skin of a patient 12, such as the steering wheel 24. The control unit 30 or computing device 70 may be adapted to continuously track electrodermal activity of the patient 12 to detect changes.

Utilizing these detected conditions from the galvanic skin sensor 49 (and other sensors 40 if included), the computing device 70 may determine aspects of the patient's health and the efficacy of treatments being applied. Sudden changes in electrodermal activity may be indicative of stress. These conditions may be utilized by the computing device 70 to adaptively configure the audio signal to match the wellbeing of the patient at any given time.

As shown in FIG. 10, the detection device 20 may comprise a tapping sensor 59 which is adapted to detect tapping strength or rates on the detection device 20 by a patient 12. The tapping sensor 59 will thus preferably be positioned on the detection device 20 at a position which the patient 12 would tap on, such as the steering wheel 24. The control unit 30 or computing device 70 may be adapted to continuously track tapping activity of the patient 12 to detect changes.

Utilizing these detected conditions from the tapping sensor 59 (and other sensors 40 if included), the computing device 70 may determine aspects of the patient's health and the efficacy of treatments being applied. Continuous tapping or sudden increases in tapping rates may be indicative of stress. These conditions may be utilized by the computing device 70 to adaptively configure the audio signal to match the wellbeing of the patient at any given time. Tapping may be used to entrain respiratory function, and heart rate, which may enhance focus and is used in dyslexia exercises.

D. Output Device

As shown in FIGS. 6-11D, an output device 50 may be utilized to audibly play the audio signal as determined by the computing device 70 in response to conditions detected by the sensors 40 of the detection device 20. The output device 50 may be communicatively interconnected with the computing device 70 so as to receive the audio signal to be played. The output device 50 may be wirelessly connected to the computing device 50 or, in some embodiments, use a wired connection. The output device 50 may be adapted to audibly play the audio signal, including various types of sounds which may incorporate binaural or isochronic tones.

Figure 4:
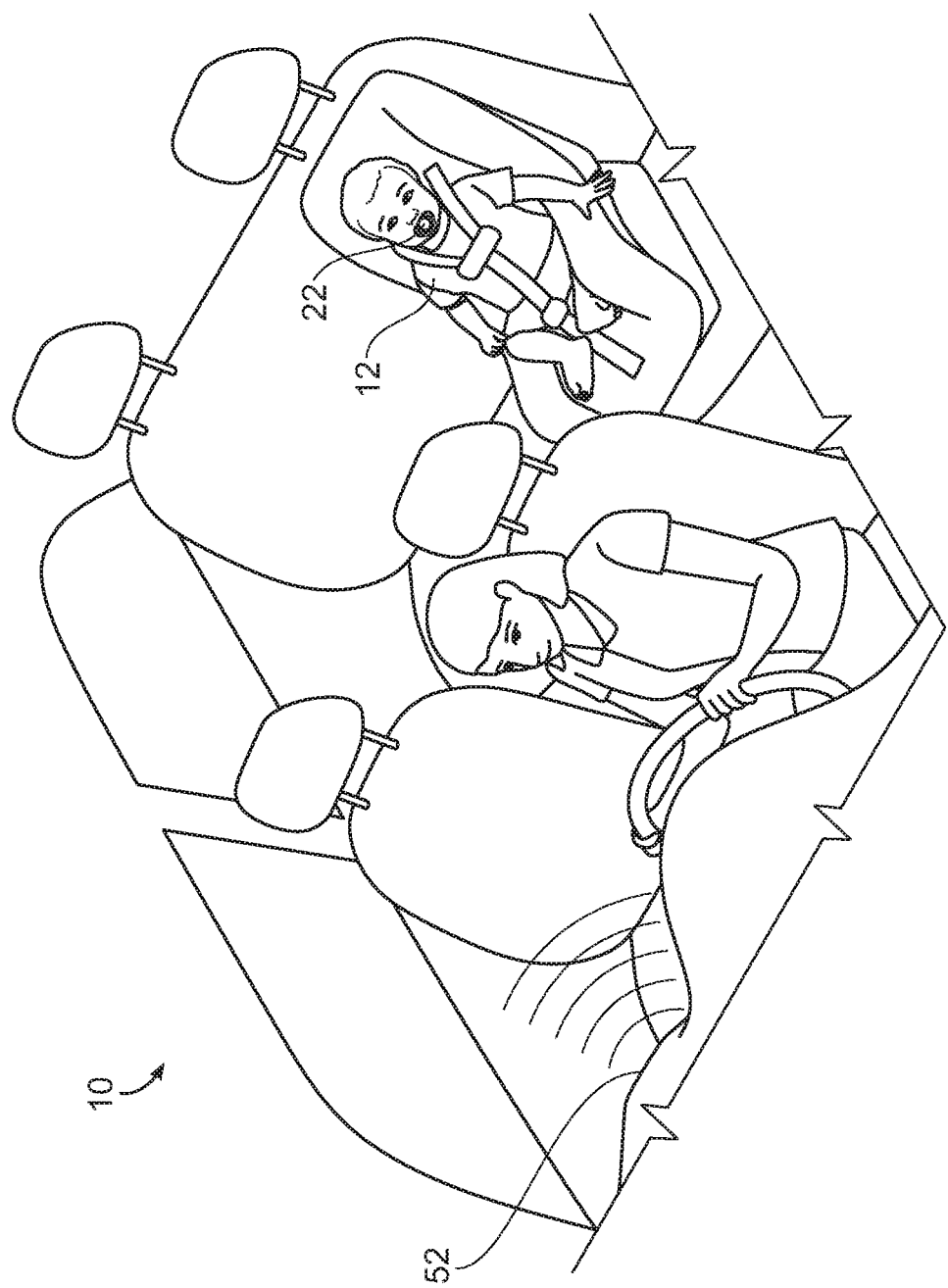
FIG. 4 is a perspective view of an adaptive audio therapy system in use with a pacifier and a speaker in a vehicle in accordance with an example embodiment.

The type of output device 50 may vary in different embodiments. Any output device 50 capable of audibly playing an audio signal may be utilized. FIGS. 1, 4, and 5 illustrate an output device 50 comprised of a speaker 52. The speaker 52 may be a stand-alone unit or may be integrated with the computing device 70, such as in embodiments in which the computing device 70 is a smart phone or tablet.

Figure 2:
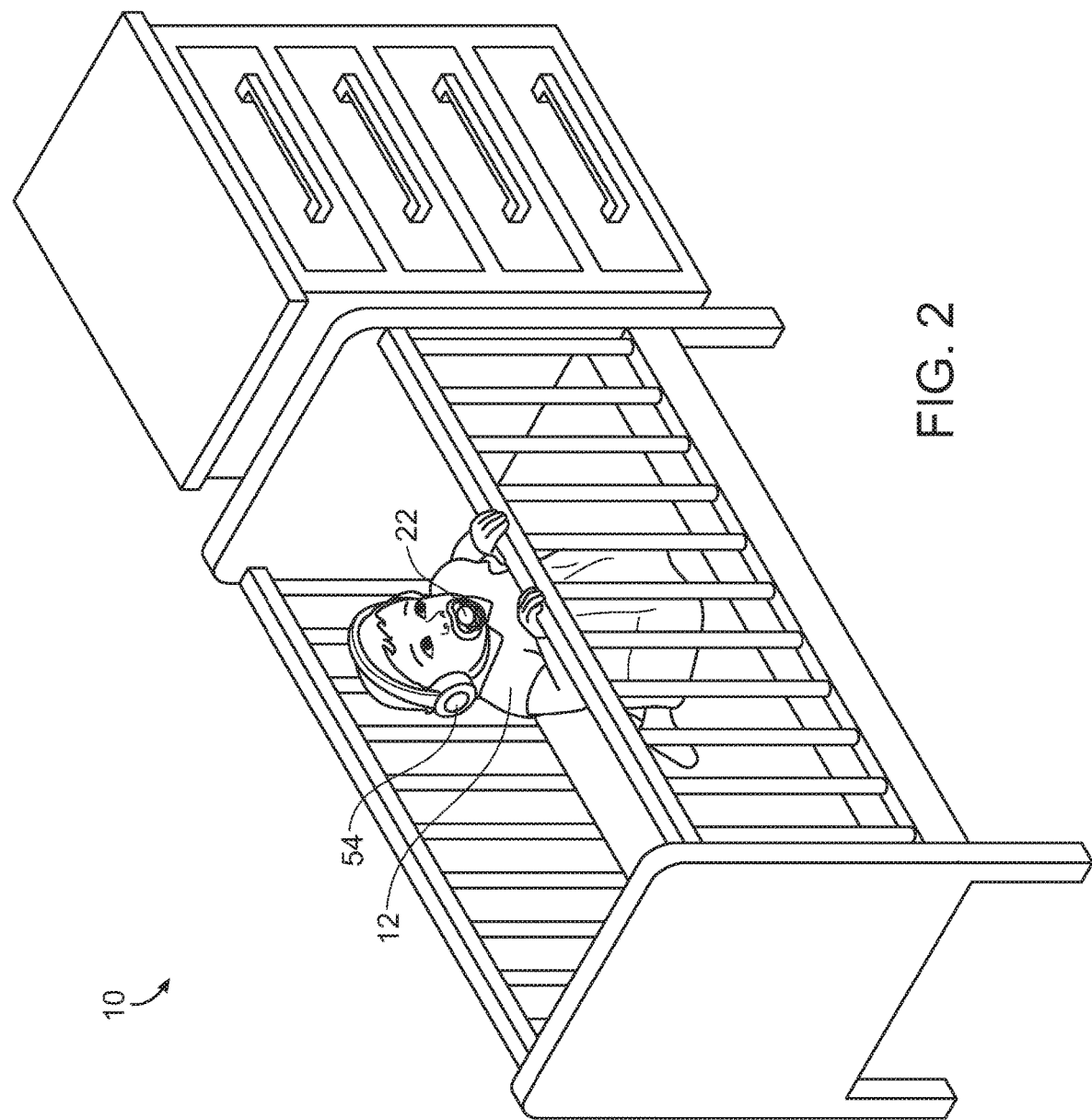
FIG. 2 is a perspective view of an adaptive audio therapy system in use with a pacifier and headphones in accordance with an example embodiment.
Figure 3:
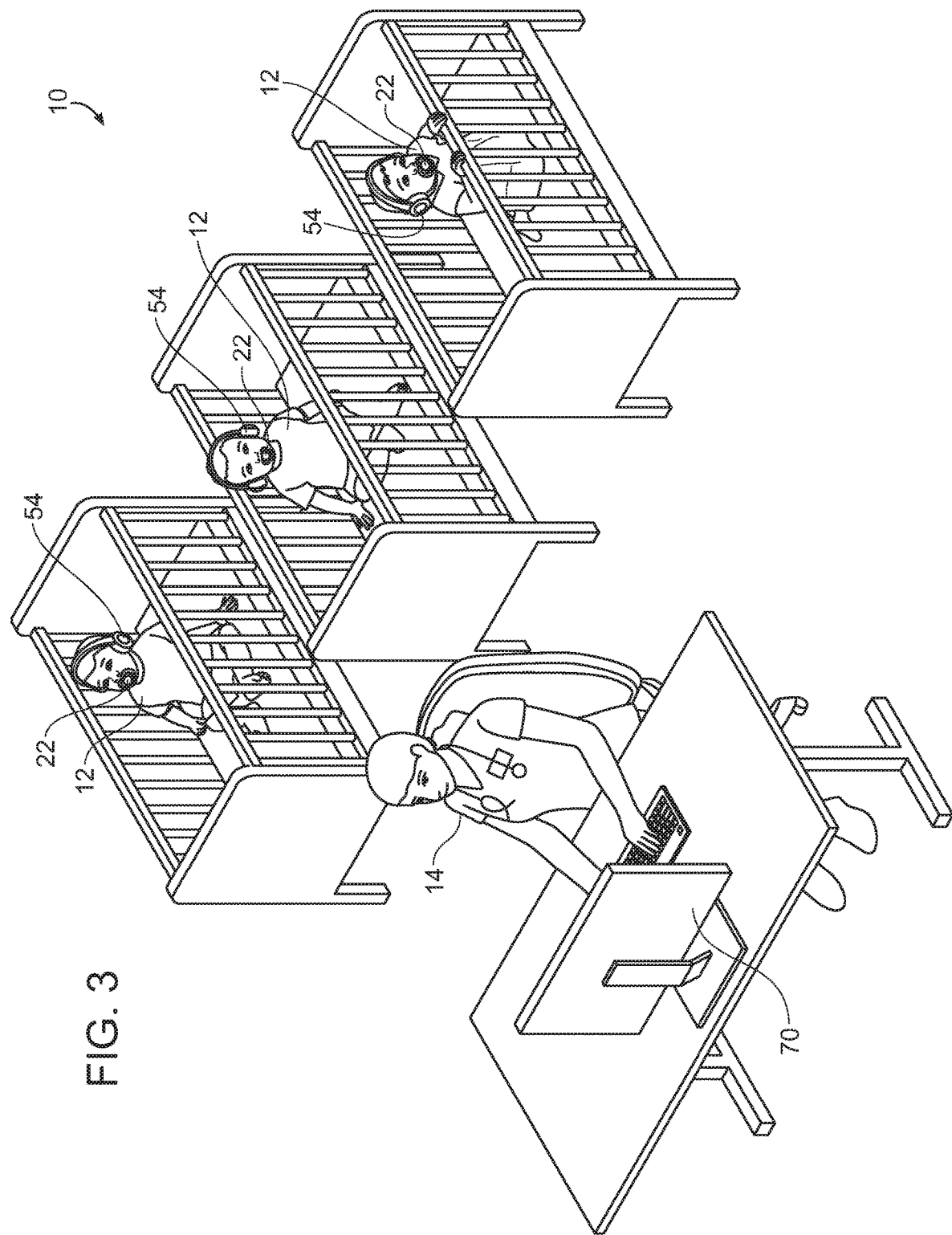
FIG. 3 is a perspective view of an adaptive audio therapy system in use with multiple pacifiers and headphones in accordance with an example embodiment.

FIGS. 2 and 3 illustrate an output device 50 comprised of headphones 54. Headphones 54 may be desirable when treating multiple patients 12 within a given space so that different audio signals may be transmitted to each different patient 12 based on each patient's 12 conditions, and efficacy of treatment such as shown in FIG. 3.

The headphones 54 are illustrated as being wireless, though wired headphones 54 may be utilized. Various types of headphones 54 may also be utilized, and the scope should not be construed as limited to the "over-the-ear" headphones 54 illustrated in the exemplary figures. For example, earbuds could be utilized in some embodiments.

E. Input Devices

Figure 6:
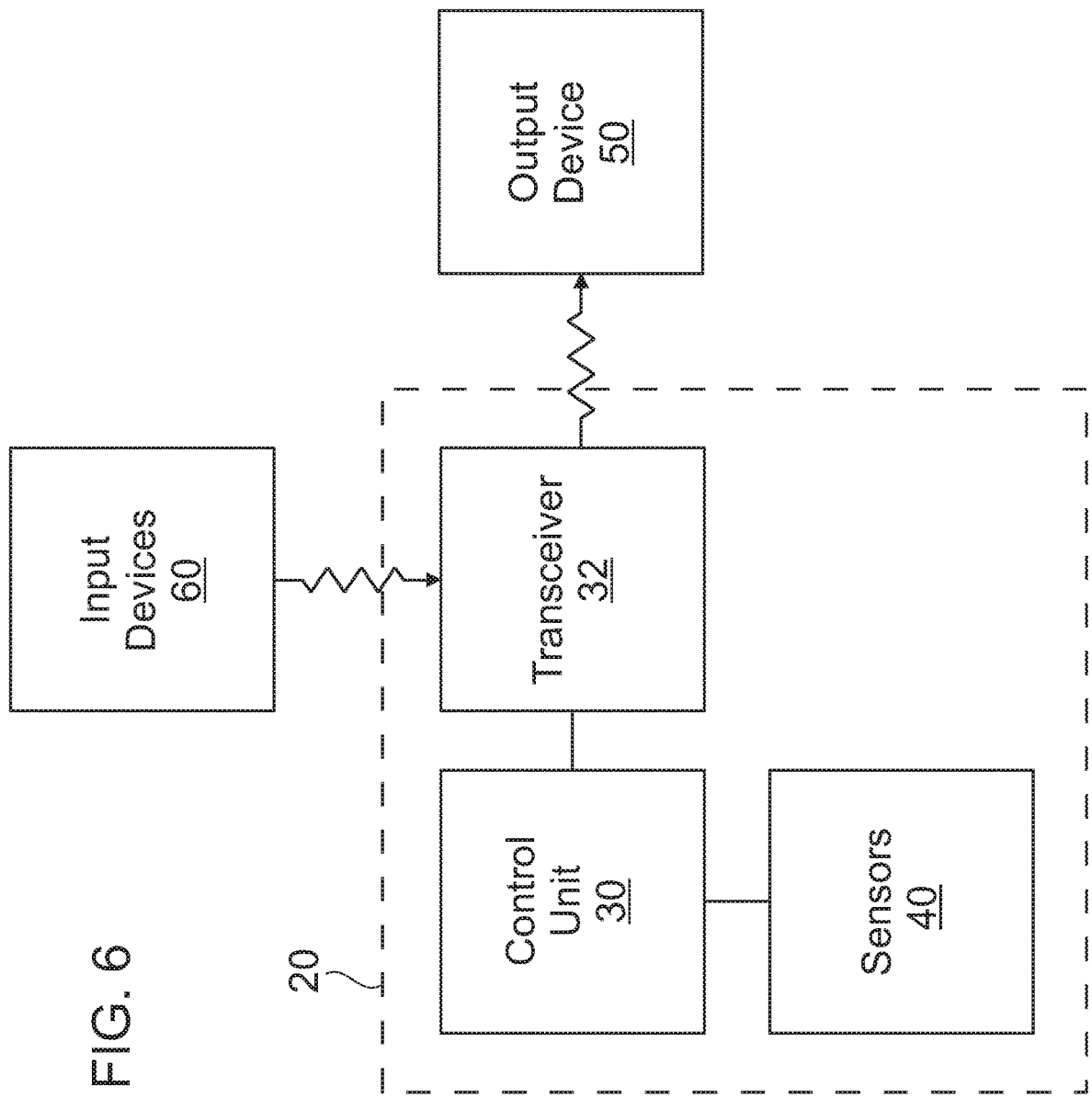
FIG. 6 is a block diagram of an adaptive audio therapy system in accordance with an example embodiment.
Figure 7:
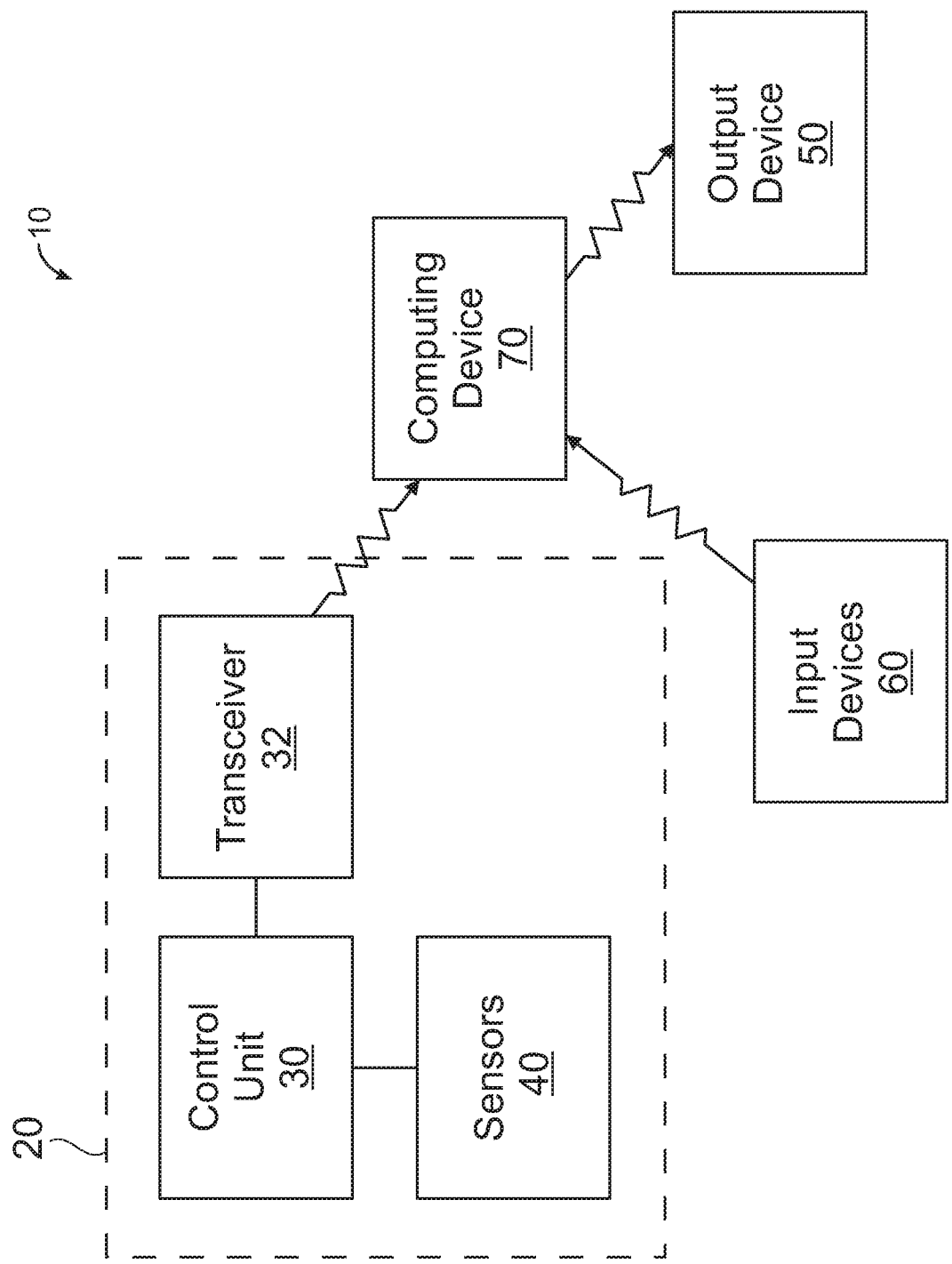
FIG. 7 is a block diagram of an adaptive audio therapy system in accordance with an example embodiment.
Figure 8:
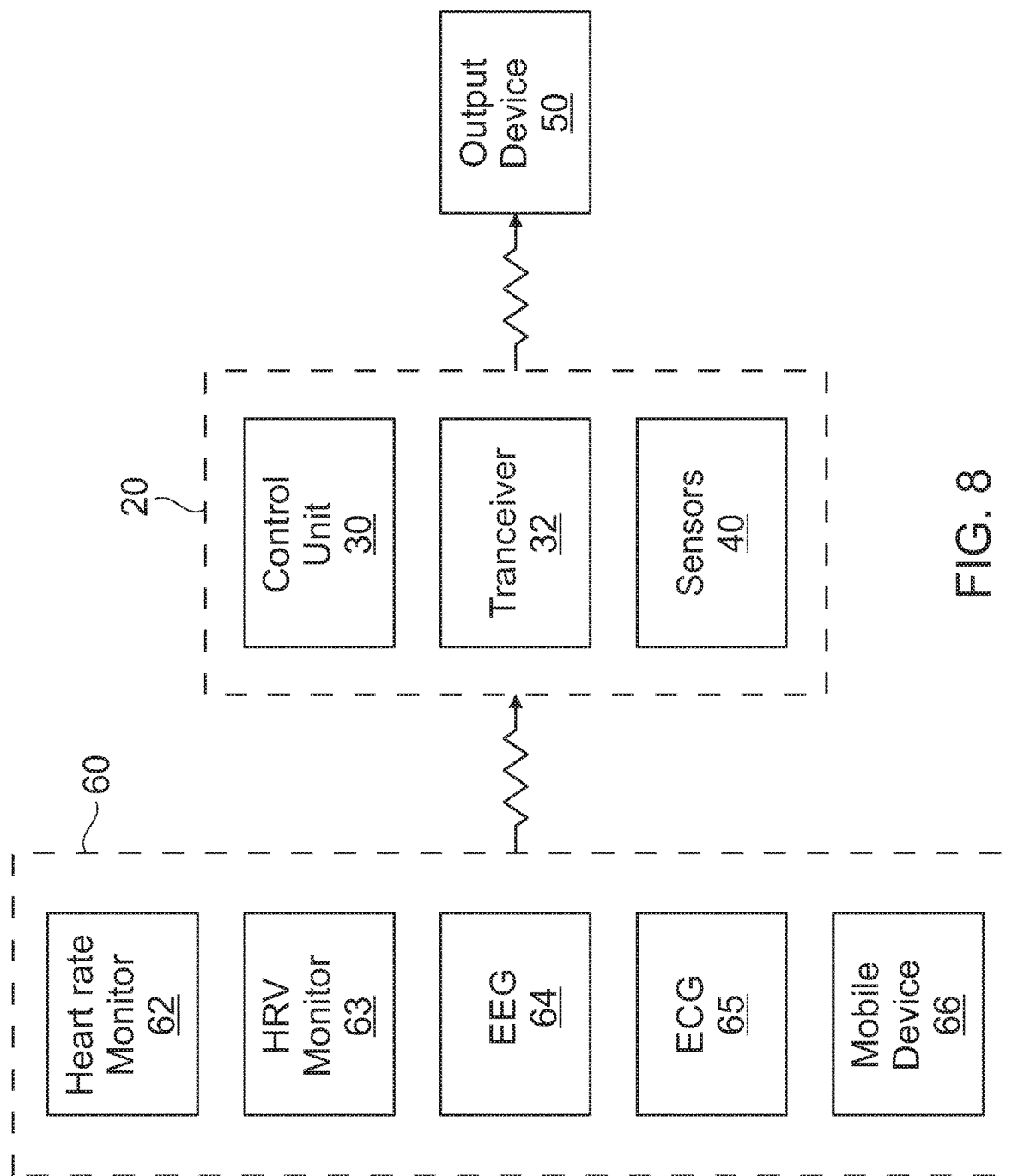
FIG. 8 is a block diagram of an adaptive audio therapy system in accordance with an example embodiment.

As shown in FIGS. 6-8, various input devices 60 may be configured to detect various conditions of the patient 12 and transmit those detected conditions to the computing device 70 for processing in real-time. In some embodiments, the input devices 60 may be integral with the computing device 70 itself. In other embodiments, the input devices 60 may be stand-alone units which are communicatively interconnected with the computing device 70.

Various types of input devices 60 known in the art to detect various conditions of a patient 12 may be utilized. FIG. 8 illustrates exemplary input devices 60 comprised of a heartrate monitor 62, heartrate variability (HRV) monitor 63, electroencephalogram (EEG) 64, electrocardiogram (ECG) 65, and/or a mobile device 66 such as a gyroscope or accelerometer. Various other medical instruments and the like may be utilized.

It may be desirable to utilize such input devices 60 when the configuration of the detection device 20 prevents certain sensors 40 from being included. For example, if the detection device 20 is not configured to read heart rate variability, an HRV monitor 63 may be communicatively connected to the computing device 70 to provide such functionality. Thus, input devices 60 may be utilized to augment missing functions of the detection device 20 for certain patients 12.

The input device 60 may comprise a mobile device 66 such as a smart phone, smart watch, FITBIT, or the like. These mobile devices 66 are commonly used by individuals and may be configured to detect certain conditions. The mobile device 66 may be communicatively interconnected with the computing device 70 to continuously transmit detected conditions in real-time. The mobile device 66 may also be configured to receive manual inputs from the patient 12. For example, the patient 12 could utilize the mobile device 66 to indicate rising stress levels if not detected by other sensors 40; with the computing device 70 processing this information and adjusting the audio signal accordingly.

F. Computing Device

As shown throughout the figures, a computing device 70 may be utilized to receive the detected conditions from the sensors 40 of the detection device 20 and/or the input devices 60. The computing device 70 may comprise a processing unit such as a microprocessor for performing various functions. The computing device 70 may comprise a storage medium to keep track of detected conditions and changes therein.

By way of example, the computing device 70 may comprise a personal computer, laptop, smart phone, tablet, or the like. The computing device 70 will generally be communicatively interconnected with the detection device 20, input device 60, and output device 50. The computing device 70 may receive the detected conditions from the detection device 20 and/or input device 60, process the conditions, and determine an appropriate audio signal such as a musical piece to treat the detected conditions of the patient 12.

Figure 11A:
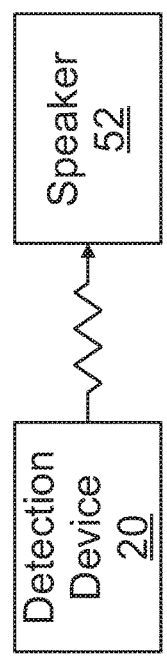
FIG. 11A is a block diagram of an adaptive audio therapy system in accordance with an example embodiment.
Figure 11B:
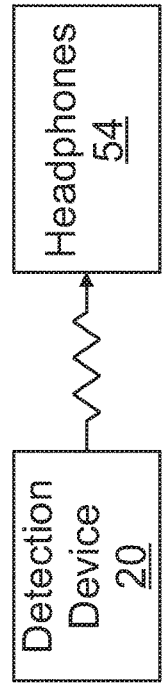
FIG. 11B is a block diagram of an adaptive audio therapy system in accordance with an example embodiment.

The audio signal will be communicated to the output device 60 to be audibly played for the patient 12. As the audio signal is played by the output device 60, the computing device 70 will continue to monitor detection conditions such as biomarkers of the patient 12. The detection conditions will then be used by the computing device 70 to maintain the efficacy of the treatment being applied, such as by selecting different audio signals or modifying/altering the existing audio signal in response to detected conditions/biomarkers. For example, a detected biomarker may suggest that the audio signal be altered for more efficient therapy, such as by altering the pitch, tuning, speed, or the like of the audio signal. In some embodiments such as shown in FIGS. 6, 11A, and 11B, the computing device 70 may be omitted, with the control unit 30 of the detection device 20 performing its functions as described below.

G. Operation of Preferred Embodiment

The manner in which the adaptive audio therapy system 10 is used may vary in different embodiments and among different types of patients 12. FIGS. 1 and 2 illustrate a detection device 20 comprised of a pacifier 22 being used to detect conditions of a patient 12 who is an infant, with the audio therapy being played by a speaker 52 in FIG. 1 and headphones 54 in FIG. 2. FIG. 3 illustrates a practitioner 14 overseeing musical therapy to three patients 12 (all infants), each having a pacifier 22 and headphones 54.

FIG. 4 illustrates a patient 12 in the backseat of a vehicle, with a pacifier 22 detecting conditions and the audio therapy being played through the vehicle's speakers 52. FIG. 5 illustrates an adult patient 12 driving a vehicle, with the steering wheel 24 serving as the detection device 20 with a pair of sensors 40 where the patient's 12 hands are held. The vehicle's speakers 52 play the audio therapy. The computing device 70 is not shown in FIG. 4, but could be comprised of a processor internal to the vehicle as is common in modern automobiles. Alternatively, the patient's 12 mobile phone or tablet may serve as the computing device 70 when driving; with the audio signal being transmitted to the vehicle's speakers 52 via BLUETOOTH or other means.

The system may be initiated by voice command in some embodiments. For example, the patient 12 could utter the phrase "Alexa, begin music therapy" or other similar phrases to automatically initiate the systems and methods described herein in a hands-free manner; particularly when driving. This may be particularly useful when a patient 12 initially did not anticipate need for audio therapy but subsequently encounters a stressful situation, such as a car crash or heavy traffic, which presents a need for audio therapy. The patient 12 in a vehicle-based embodiment would be able to sue the voice command interface to initiate the system without having to pull over and navigate menus/options on a screen.

It should be appreciated that these are merely exemplary embodiments meant to serve as examples of usage of the adaptive audio therapy system 10. Various other types of detection devices 20 and output devices 50 may be utilized. The adaptive audio therapy system 10 may be utilized to provide therapy to a single individual or to multiple patients 12. While FIG. 3 illustrates a practitioner 14 such as a musical therapist, such an individual is not necessarily needed; with the computing device 70 providing the same functionality instead of a practitioner 14.

It should also be appreciated that the processing of condition data and the decision-making to select appropriate audio therapies may be performed in various manners in different embodiments. FIG. 11A illustrates that the detection device 20 communicates directly with the speaker 52; with a control unit 30 of the detection device 20 processing data from the sensors 40 and selecting/outputting the audio signal directly to the speaker 52. FIG. 11B illustrates a similar embodiment in which headphones 54 are utilized instead of speakers 52.

Figure 11C:
FIG. 11C is a block diagram of an adaptive audio therapy system in accordance with an example embodiment.
Figure 11D:
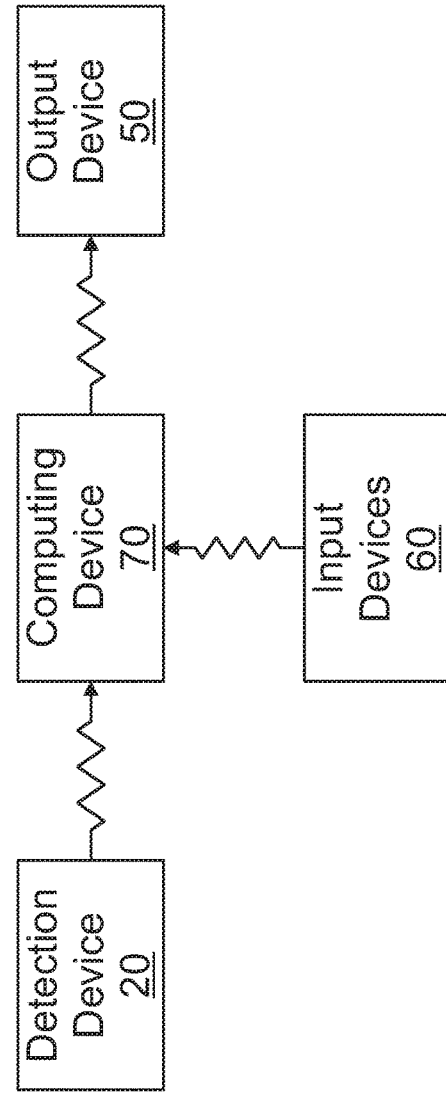
FIG. 11D is a block diagram of an adaptive audio therapy system in accordance with an example embodiment.

FIGS. 11C and 11D illustrate embodiments which utilize a computing device 70; with the detection device 20 communicating detected conditions from its sensors 40 to the computing device 70, which in turn processes the data and continuously determines/modifies an appropriate audio signal to be played by the output device 50. FIG. 11D illustrates that the computing device 70 may receive additional conditions of the patient 12 from various input devices 60 as discussed previously.

FIG. 12 illustrates an exemplary method of condition detection. The detection device 20 is first put in physical contact with the patient 12. For example, a pacifier 22 may be given to an infant who will suck on it as normal, or a steering wheel 24 may serve as the detection device 20, with an individual 12 placing her hands on the steering wheel 24 as is normal when driving.

While the detection device 20 is in contact with the individual 12, the sensors 40 will continuously and automatically detect various conditions of the individual 12 such as heart rate, respiration rate, oxygen saturation levels, and so on. As these conditions are being detected, the detection device 20 will continuously in real-time transmit the detected conditions to the computing device 70.

Figure 13:
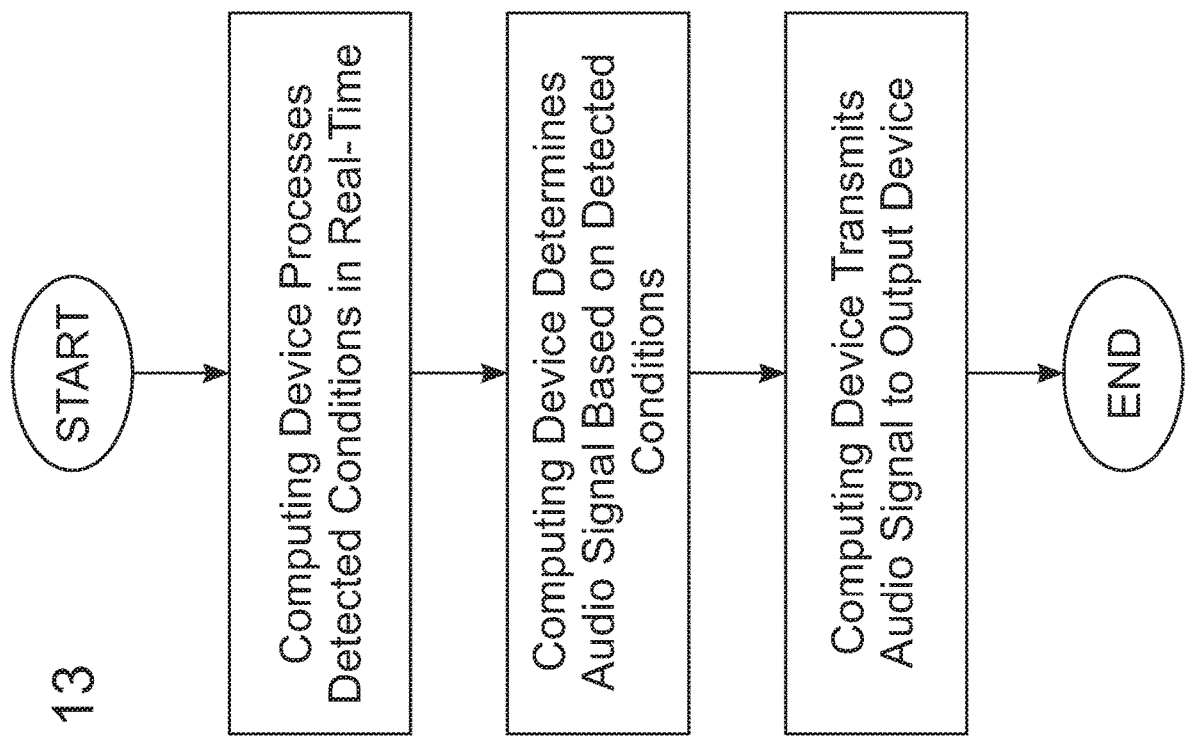
FIG. 13 is a flowchart illustrating audio signal determination and transmission of an adaptive audio therapy system in accordance with an example embodiment.

FIG. 13 illustrates an exemplary method of processing the detected conditions received from the detection device 20 by the computing device 70. The computing device 70 processes the detected conditions received from the detection device 20 in real-time; continuously determining an appropriate audio signal based on the detected conditions. For example, the computing device 70 may modulate the audio signal (such as tempo or pitch) based on the detected conditions. The computing device 70 may also substitute one type of audio therapy for another by, for example, transitioning from music to nature sounds or the like, based on the detected conditions.

By way of example, the tempo of the audio therapy may be interpolated to be matched or entrained with the heart rate, respiratory function, or brain-waves of the patient 12. The patient 12 may experience heartrate entrainment, following the tempo change of the curated audio therapy (such as music). The computing device 70 will continuously in real-time deliver medically and emotionally relevant sounds or music based on the detected conditions by the detection device 20.

The system may also be configured to inform a practitioner 14 of alterations of physiological data over time. Patients 12 may be asked to complete an efficacy rating questionnaire to personalize treatment and increase efficacy of future treatments. This information may also be anonymized and then utilized in further research. This function may be utilized to predict illness onset (preventative medicine). Physiological data, such as movement patterns, may inform the computing device 70 which assembles dedicated playlists of audio therapy according to the patient's 12 tastes and the symptoms/detected conditions of the patient 12. Data may be stored by the computing device 70, such as in an external or internal storage medium, so that results may be tracked and the computing device 70 may adapt to specific patients 12.

FIG. 14 illustrates an exemplary method of providing audio therapy utilizing an exemplary embodiment of the adaptive audio therapy system 10. The computing device 70 may receive detected conditions from the sensors 40 of the detection device 20. If utilized, the computing device 70 may also receive detected conditions from input devices 60. The computing device 70 may process the detected conditions (both from the detection device 20 and the input devices 60, if any) to determine an appropriate audio signal based on the detected conditions and, if available, tastes of the patient 12. The computing device 70 will then transmit the audio signal to the output device 50 to be played or, in some embodiments, may play the audio signal itself.

As therapy is provided, the computing device 70 will continuously in real-time receive condition data and adjust the audio therapy appropriately. By way of example, the computing device 70 will detect when biomarkers or conditions of the patient 12 vary during application of the therapy. In response to variations or changes in the biomarkers or conditions detected by the detector 20 and transmitted to the computing device 70, the computing device 70 may either select a different audio signal or made modifications/alterations to the existing audio signal. For example, the computing device 70 may modulate the pitch or tempo of an existing audio signal to reflect changing patient 12 conditions or biomarkers, or to entrain the audio signal with a detected condition of the patient 12, such as heartrate or respiration. Binaural or isochronic tones may be incorporated into the audio signal or removed therefrom based on the efficacy of such tones as detected by the detector 20 and transmitted to the computing device 70.

Unless otherwise defined, all technical and scientific terms used herein have the same meaning as commonly understood by one of ordinary skill in the art to which this invention belongs. Although methods and materials similar to or equivalent to those described herein can be used in the practice or testing of the adaptive audio therapy system, suitable methods and materials are described above. All publications, patent applications, patents, and other references mentioned herein are incorporated by reference in their entirety to the extent allowed by applicable law and regulations. The adaptive audio therapy system may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. An adaptive audio therapy system, comprising:
a detection device adapted to make physical contact with an individual, the detection device comprising a plurality of sensors for detecting at least one condition of the individual, wherein the detection device is comprised of a pacifier, wherein the plurality of sensors is comprised of an oxygen saturation sensor for detecting oxygen saturation of the individual, a temperature sensor for detecting a temperature of the individual, a heart rate sensor for detecting a heart rate of the individual, a heart rate variability sensor for detecting a heart rate variability of the individual, a respiration sensor for detecting respiration of the individual, and a movement sensor for detecting movement of the individual;
a computing device communicatively interconnected with the detection device for processing detection data received from the plurality of sensors of the detection device, the computing device being adapted to automatically identify an audio signal based on the at least one condition detected by one or more of the plurality of sensors of the detection device; and
an output device for audibly playing the audio signal in real-time.

2. The adaptive audio therapy system of claim 1, wherein the output device comprises a speaker.

3. The adaptive audio therapy system of claim 1, wherein the plurality of sensors further comprises a suction sensor for detecting attributes of a sucking motion applied to the pacifier by the individual.

4. The adaptive audio therapy system of claim 3, wherein the computing device is adapted to automatically identify the audio signal based on the sucking motion applied to the pacifier by the individual.

5. The adaptive audio therapy system of claim 1, wherein the audio signal is comprised of music.

6. The adaptive audio therapy system of claim 1, wherein the detection device comprises a control unit for controlling communication of the detected conditions to the computing device.

7. The adaptive audio therapy system of claim 1, wherein the control unit comprises a microprocessor.

8. An adaptive audio therapy system, comprising:
a detection device adapted to make physical contact with an individual, the detection device comprising a plurality of sensors for detecting a plurality of first conditions of the individual, wherein the detection device is comprised of a pacifier, wherein the plurality of sensors is comprised of an oxygen saturation sensor for detecting oxygen saturation of the individual, a temperature sensor for detecting a temperature of the individual, a heart rate sensor for detecting a heart rate of the individual, a heart rate variability sensor for detecting a heart rate variability of the individual, a respiration sensor for detecting respiration of the individual, and a movement sensor for detecting movement of the individual;
a computing device communicatively interconnected with the detection device for processing detection data received from the plurality of sensors of the detection device, the computing device being adapted to automatically identify an audio signal based on the first conditions detected by the plurality of sensors of the detection device;
an input device communicatively connected to the computing device, the input device being adapted to detect a plurality of second conditions of the individual, wherein the computing device is adapted to automatically identify the audio signal based on both the first conditions detected by the sensors and the second conditions detected by the input device; and
an output device for audibly playing the audio signal in real-time.

9. The adaptive audio therapy system of claim 8, wherein the input device is selected from the group consisting of a heartrate monitor, a heartrate variability monitor, an electroencephalogram, an electrocardiogram, and a mobile device.

* * * * *